(12) United States Patent
Van Schravendijk et al.

(10) Patent No.: US 10,400,042 B2
(45) Date of Patent: Sep. 3, 2019

(54) METHOD FOR INCREASING PYRO-GLUTAMIC ACID FORMATION OF A PROTEIN

(71) Applicant: MABXIENCE S.A., Montevideo (UY)

(72) Inventors: Marie Rose Van Schravendijk, Worcester, MA (US); Stephen Waugh, Bothell, WA (US); Barbara Thorne, Sammamish, WA (US)

(73) Assignee: MABXIENCE RESEARCH, S.L., Madrid (ES)

( * ) Notice: Subject to any disclaimer, the term of this patent is extended or adjusted under 35 U.S.C. 154(b) by 376 days.

(21) Appl. No.: 14/780,964

(22) PCT Filed: Apr. 3, 2014

(86) PCT No.: PCT/EP2014/056700
§ 371 (c)(1),
(2) Date: Sep. 28, 2015

(87) PCT Pub. No.: WO2014/161940
PCT Pub. Date: Oct. 9, 2014

(65) Prior Publication Data
US 2016/0060349 A1 Mar. 3, 2016

(30) Foreign Application Priority Data
Apr. 4, 2013 (EP) .................................... 13162241

(51) Int. Cl.
*C07K 1/18* (2006.01)
*C07K 1/34* (2006.01)
*C07K 16/28* (2006.01)

(52) U.S. Cl.
CPC ............ *C07K 16/2887* (2013.01); *C07K 1/18* (2013.01); *C07K 1/34* (2013.01); *C07K 2317/14* (2013.01); *C07K 2317/24* (2013.01); *C07K 2317/40* (2013.01)

(58) Field of Classification Search
None
See application file for complete search history.

(56) References Cited

U.S. PATENT DOCUMENTS

2006/0121032 A1 6/2006 Dahiyat et al.
2010/0099142 A1* 4/2010 Norby ...................... C12N 9/48
435/68.1

FOREIGN PATENT DOCUMENTS

| CN | 102492040 A | 6/2012 | |
|---|---|---|---|
| JP | 2007/514423 A | 6/2007 | |
| RU | 2007 106050 | 8/2008 | |
| WO | WO-2004099249 A2 * | 11/2004 | ............ C07K 16/00 |
| WO | WO 2005/059127 A1 | 6/2005 | |
| WO | WO 2006/007853 A2 | 1/2006 | |
| WO | WO 2006/024497 A1 | 3/2006 | |
| WO | WO 2007/064911 A1 | 6/2007 | |
| WO | WO 2009/058812 A1 | 5/2009 | |
| WO | WO 2010/138184 A2 | 12/2010 | |

OTHER PUBLICATIONS

Low et al. "Future of antibody purificaiton" Journal of Chromatography B, 848, 48-63 (Year: 2007).*
Shukla et al. "Downstream processing of monoclonal antibodies—Application of platform approaches" Journal of Chromatography B, 848 28-39 (Year: 2007).*
International Search Report and Written Opinion of the International Searching Authority for International application No. PCT/EP2014/056700 dated Jul. 10, 2014, 12 pages.
Chadd, H. et al., "Therapeutic antibody expression technology", Current Opinion Biotechnology, Apr. 1, 2001, vol. 12, pp. 188-194.
Chelius, D. et al., "Formation of Pyroglutamic Acid from N-Terminal Glutamic Acid in Immunoglobulin Gamma Antibodies", Anal. Chem., Apr. 1, 2006, vol. 78, No. 7, pp. 2370-2376.
Dick, L.et al., "Determination of the Origin of the N-Terminal Pyro-Glutamate Variation in Monoclonal Antibodies Using Model Peptides", Biotechnology and Bioengineering, Jun. 15, 2007, vol. 97, No. 3, pp. 544-553.
Gadgil, H. et al., "Improving mass accuracy of high performance liquid chromatography/electrospray ionization time-of-flight mass spectrometry of intact antibodies", J. Am. Soc. Mass Spectrom, Feb. 28, 2006, vol. 17, pp. 867-872.
Kumar, A. et al., "Pyroglutamic acid: throwing light on a lightly studied metabolite", Current Science, Jan. 25, 2012, vol. 102, No. 2, pp. 288-297.
Lyubarskaya, Y. et al., "Analysis of recombinant monoclonal antibody isoforms by electrospray ionization mass spectrometry as a strategy for streamlining characterization of recombinant monoclonal antibody charge heterogeneity", Analytical Biochemistry, Jan. 1, 2006, vol. 348, pp. 24-39.
Needleman, S. et al., "A General Method Applicable to the Search for Similarities in the Amino Acid Sequence of Two Proteins", J. Mol. Biol., Mar. 10, 1970, vol. 48, No. 3, pp. 443-453.
Ouellette, D. et al., "Studies in serum support rapid formation of disulfide bond between unpaired cysteine residues in the $V_H$ domain of an immunoglobulin G1 molecule", Anal Biochem., Feb. 2010, vol. 397, pp. 37-47.

(Continued)

*Primary Examiner* — Daniel E Kolker
*Assistant Examiner* — James L Rogers
(74) *Attorney, Agent, or Firm* — Squire Patton Boggs (US) LLP

(57) ABSTRACT

A method for conversion of an N-terminal glutamine and/or glutamic acid residue of a protein to pyro-glutamic acid within a purification process.

Figure 1:
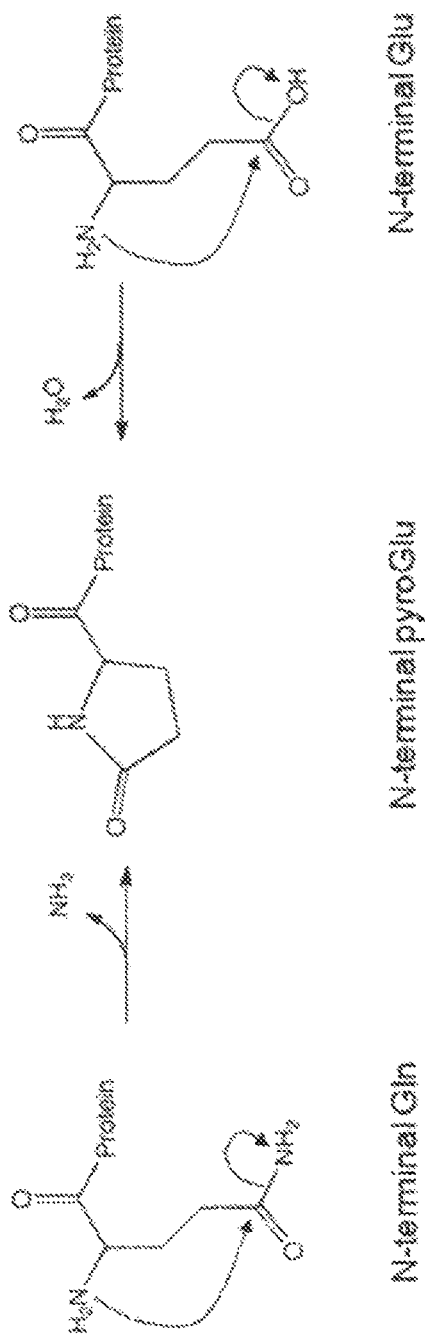

16 Claims, 7 Drawing Sheets
Specification includes a Sequence Listing.

(56) References Cited

OTHER PUBLICATIONS

Rice, P. et al., "EMBOSS: The European Molecular Biology Open Software Suite", TIG, Jun. 2000, vol. 16, No. 6, pp. 276-277.
Rink, R. et al., "To protect peptide pharmaceuticals against peptidases", Journal of Phamlacollogical and Toxicollogical Methods, Mar.-Apr. 2010, vol. 61, pp. 210-218.
Schilling, S. et al., "Glutaminyl cyclases unfold glutamyl cyclase activity under mild acid conditions", FEBS Letters, Apr. 9, 2004, vol. 563, pp. 191-196.
Xu, W. et al., "Method to convert N-terminal glutamine to pyroglutamate for characterization of recombinant monoclonal antibodies", Anal Biochem., May 1, 2013, vol. 436, pp. 10-12.
Yu, L. et al., "Investigation of N-terminal glutamate cyclization of recombinant monoclonal antibody in formulation development", Journal of Pharmaceutical and Biomedical Analysis, Oct. 11, 2006, vol. 42, pp. 455-463.
Liu, Hui F., et al., "Recovery and purification process development for monoclonal antibody production", Sep. 2010, mAbs, vol. 2, Issue 5, pp. 480-499.
Shukla, Abhinav A., et al., "Downstream processing of monoclonal antibodies—Application of platform approaches", Journal of Chromatography B, Oct. 13, 2006, vol. 848, pp. 28-39.
Wang, Bo, et al., "Structural comparison of two anti-CD20 monoclonal antibody drug products using middle-down mass spectrometry", Analyst, Apr. 3, 2013, vol. 138, No. 10, pp. 3058-3065.
Iyer, Harish, et al., "Considerations During Development of a Protein A-Based Antibody Purification Process", Jan. 2002, BioPharm, pp. 14-20, and p. 53.
Kelly, Brian, "Industrialization of mAb production technology: The bioprocessing industry at a crossroads", Sep.-Oct. 2009, mAbs vol. 1, No. 5, pp. 443-452; DOI: 10.4161.mabs.1.5.9448.

* cited by examiner

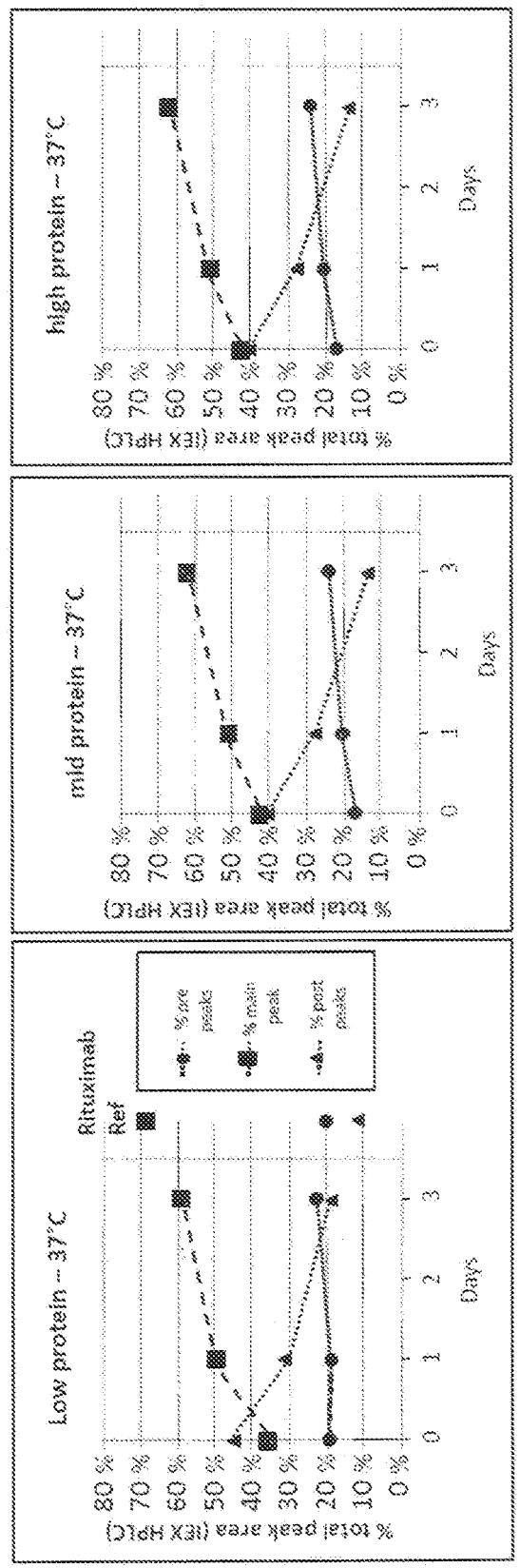

METHOD FOR INCREASING PYRO-GLUTAMIC ACID FORMATION OF A PROTEIN

FIELD OF THE INVENTION

The invention relates to a method for the conversion of an N-terminal glutamine and/or glutamic acid residue of a protein to pyro-glutamic acid within a purification process. Moreover, the present invention also relates to a method for the purification of a protein containing an N-terminal pyro-glutamic acid. The methods of the present invention may be included in a manufacturing process for preparing a protein having an N-terminal pyro-glutamic acid, in particular for preparing an active pharmaceutical ingredient (API) for a pharmaceutical product.

BACKGROUND OF THE INVENTION

The majority of recombinant therapeutic proteins display one or more post-translational modifications. These modifications may occur during their ribosomal synthesis or (more usually) after synthesis is complete. A large number of post-translational modifications have been characterized to date, and these modifications may impart some structural aspect or functional role of the affected protein. Common post-translational modifications associated with therapeutic proteins include carboxylation and hydroxylation, amidation and sulfation, disulfide bond formation and proteolytic processing, as well as glycosylation, isomerization, oxidation, cyclization of a N-terminal glutamine or glutamic acid to pyro-glutamic acid, fragmentation, and aggregation. Thus, post-translational modifications may either be caused by enzymatic modification of the protein or by non-enzymatic conversion and post-translational modifications may occur inside the expression host, during cell culture, or during purification or storage of the protein.

Recombinant monoclonal antibodies are becoming of great value for the biotechnology industry and numerous antibodies have been approved for treating a variety of diseases. As antibodies generally are produced in mammalian cells, such as CHO cells, they may have a number of different post-translational modifications, which lead to heterogeneity in the product. Heterogeneity may be caused by changes in the surface charge of the antibody, either directly, as a change in the number of charged residues, or indirectly as a chemical or physical alteration that changes surface-charge distribution such as glycosylation, carboxypeptidase clipping of the C-terminal lysine of the heavy chain, and cyclization of a N-terminal glutamine or glutamic acid residue to pyro-glutamic acid.

Antibodies are typically made of basic structural units, each with two large heavy chains and two small light chains joined via disulfide bridges and non-covalent interactions. There are several different types of antibody heavy chains, and several different kinds of antibodies, which are grouped into different isotypes based on which heavy chain they possess. For example there are four isotypes of human IgG (1 through 4), depending on the gene for the heavy chain constant region. The light chain constant domain is coded by two genes (κ or λ). Consequently, each IgG isotype can be either κ or λ, for instance IgG1κ. Although there are several types of antibodies produced in different types of cell lines the most clinically significant antibodies are full-length antibodies of the IgG1 or IgG2 types.

Many of the human IgG1 or IgG2 types antibodies contain a glutamic acid (Glu) and/or a glutamine (Gln) residue at the N-terminus of either the light chain or the heavy chain or both. A significant portion of light chain genes codes for either glutamic acid or glutamine. Such N-terminal glutamic acid and/or glutamine residues may undergo cyclization to form pyro-glutamate (pGlu) as shown in FIG. 1. Pyro-glutamate formation therefore occurs in virtually all clinically significant antibodies and different levels of completeness of the process are a common source of heterogeneity. This heterogeneity is not desired in therapeutic antibodies, since these changes can alter surface charge properties of the antibody either directly by changing the number of charged groups or indirectly by introducing structural alterations. Such modifications have the potential to decrease biological activity, as well as alter pharmacokinetics and antigenicity.

During cyclization of glutamine, the N-terminal primary amine (positively charged at a neutral pH) is converted to a neutral amide, resulting in a change of the net charge of the antibody. The reaction is accompanied by a loss of ammonia (17 Da). Consequently, the lack of cyclization may be detected as basic variants by cation exchange chromatography, since the main peak is typical the fully cyclized species or as late-eluting peaks by reversed-phase HPLC due to the increased hydrophobicity after the loss of the N-terminal amine.

Cyclization of glutamic acid occurs via the carboxyl group of the side chain and the N-terminal amine, thus forming a neutral amide and releasing water (18 Da). The net charge remains the same because one acidic and one basic group condense in the reaction, however, the loss of two charged residues increases the hydrophobicity of the molecule, allowing detection by reversed-phase HPLC.

The mechanism of pyro-glutamic acid formation in antibodies is not fully understood. Cyclization can occur spontaneously or it can be aided by an enzyme glutaminyl cyclase. It remains unclear whether glutaminyl cyclase is active in the CHO cell line, which is most commonly used for antibody production; however, rates of spontaneous cyclization indicate that the reaction is likely non-enzymatic.

For instance Yu et al. (Journal of Pharmaceutical and Biomedical Analysis 2006; 42:455-463) investigated the non-enzymatic pyro-glutamate formation from glutamic acid (Glu or E) at the N-terminus of both the light chain and the heavy chain of a monoclonal antibody for a period of 3 months. Yu et al. states that this non-enzymatic cyclization of Glu to pGlu of mAbs could be one of the major degradation pathways incurred in the mAb production and storage depending on pH and temperature conditions during the process development. They concluded that whether such pyro-Glu may induce further modifications and alter the mAb bioactivity or therapeutic potency is unclear, and they proposed to closely monitoring N-terminal pGlu formation since it can be critical to ensure quality of mAb therapeutics with N-terminal Glu.

Chelius et al. (Anal. Chem. 2006, 78, 2370-2376) also investigated the non-enzymatic pyro-glutamate formation from glutamic acid at the N-terminus of both the light chain and the heavy chain of several monoclonal antibodies and found that this non-enzymatic reaction does occur very commonly and can be detected after a few weeks of incubation at 37° C. and 45° C. The rate of this reaction was measured in several aqueous buffers with different pH values, showing minimal formation of pyro-glutamic acid at pH 6.2 and increased formation of pyro-glutamic acid at pH 4 and pH 8.

Having regard to the conversion of glutamine (Gln or Q) to pyro-glutamate Dick et al. (Biotechnology and Bioengineering, Vol. 97, No. 3, Jun. 15, 2007) showed that such cyclization of the N-terminal glutamine of a recombinant monoclonal antibody occurs spontaneously and concluded that the near complete conversion observed in many final container monoclonal antibodies is most likely caused by a combination of bioreactor incubation and purification conditions with a majority of the modification occurring in the bioreactor. This study proves that the commonly observed pyro-Q variant in many recombinant antibodies is caused inside the bioreactor with only a small contribution from the purification process, and is accelerated by high temperature and solvent composition. Specifically, the higher conversion is found at 37° C. and in a 35 mM phosphate buffer with 75 mM NaCl (pH 6.2).

Thus, post-translational modifications such as cyclization of N-terminal glutamine or glutamic acid residue to pyro-glutamic acid lead to heterogeneity of the expressed protein that may differ from batch to batch due to slight variations in production and purification conditions. Therefore, one of the more difficult challenges for producing a biosimilar protein is to match the heterogeneity of the innovator product. So, a more robust and reproducible industrial large-scale purification process with analytical support is needed to satisfy the stringent purity requirements for pharmaceutical proteins, such as antibodies.

SUMMARY OF THE INVENTION

A first aspect of the invention relates to a method for the conversion of an N-terminal glutamine and/or glutamic acid residue of a protein to pyro-glutamic acid within a purification process, comprising the step of incubating the protein under conditions to promote cyclization of the N-terminal glutamine and/or glutamic acid residue.

A second aspect of the invention relates to a method for the purification of a protein containing an N-terminal glutamine and/or glutamic acid residue, the method comprising a step of conversion of the N-terminal glutamine and/or glutamic acid residue of said protein to N-terminal pyro-glutamic acid. Such conversion is done under conditions to promote cyclization of the N-terminal glutamine and/or glutamic acid residue.

A third aspect of the present invention relates to a method of preparing a protein having an N-terminal pyro-glutamic acid as an API for a pharmaceutical product, the method comprising a purification method of any one of the first or second aspects as well as embodiments thereof.

An object of the present invention is to provide an alternative process of preparing a protein having increased or controlled N-terminal pyro-glutamic acid levels in order to reduce or obtain desired product heterogeneity.

The present inventors have found that by introducing a step of incubation/conversion of N-terminal glutamine and/or glutamic acid residues to pyro-glutamic acid during the purification process of a protein having an N-terminal glutamine and/or glutamic acid residue, in particular of a monoclonal antibody, the level of heterogeneity can be manipulated to desired levels.

Further objects of the present invention will become apparent upon reading the present description, Figures and claims.

Definitions

The term "identity" as used herein refers to the relatedness between two amino acid sequences or between two nucleotide sequences and is described by the parameter "sequence identity". For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows: (Identical Residues×100)/(Length of Alignment−Total Number of Gaps in Alignment).

The term "N-terminal", "N-terminus" or "amino-terminus" as used herein refers to a free amine group (—NH$_2$) in the terminal part of a protein or polypeptide. The usual way of writing a protein or polypeptide sequence is to put the N-terminus on the left and write the sequence from N- to C-terminus. When the protein or polypeptide is translated from messenger RNA, it is created from N-terminus to C-terminus.

The term "glutamine", "2-Amino-4-carbamoylbutanoic acid", "Gln" or "Q" as used herein is one of the 20 amino acids encoded by the standard genetic code. Its side-chain is an amide formed by replacing the side-chain carboxyl of glutamic acid with an amide functional group. Therefore, it can be considered the amide of glutamic acid.

The term "glutamic acid", "2-Aminopentanedioic acid", "Glu" or "E" as used herein is one of the 20 amino acids encoded by the standard genetic code. The side chain carboxylic acid functional group exists in its negatively charged deprotonated carboxylate form at physiological pH.

The term "polypeptide" as used herein refers to a single linear chain of amino acid monomers linked by peptide bonds. Amino acids which, have been incorporated into a polypeptide are termed "residues"; every polypeptide has one N-terminus and one C-terminus residue at the respective ends of the polypeptide. Polypeptides as used herein are longer peptides that comprise more than about 20 consecutive amino acids.

The term "protein" as used herein refers to biochemical compounds consisting of one or more polypeptides typically folded into a globular or fibrous form, facilitating a biological function. A protein may be linked by bonds other than peptide bonds, for example, such polypeptides making up the protein may be linked by disulfide bonds. The term "protein" as used herein is intended to encompass antibodies, fragments of proteins and antibodies, cleaved forms of proteins and antibodies, and the like, which are greater than about 20 consecutive amino acid residues. Moreover, protein as used herein is intended to encompass naturally occurring polypeptides and recombinantly produced polypeptides.

The term "pyro-glutamic acid", "5-oxoproline", "pidolic acid", or "pyro-glutamate" as used herein refers broadly to an uncommon amino acid derivative in which the free amino group of glutamic acid or glutamine cyclizes to form a lactam. It is found in many proteins (e.g bacteriorhodopsin, fibrin, fibrinogen), neuronal peptides and hormones (e.g. Neurotensin, Gastrin, Apelin and Orexin A) and antibodies (e.g. Infliximab, Cetuximab, Rituximab, Trastuzumab, Bevacizumab, Panitumumab, Adalimumab, Ranibizumab). N-terminal glutamine and glutamic acid residues can spontaneously cyclize to become pyro-glutamate. This is one of several forms of blocked N-terminals, which present a problem for N-terminal sequencing using Edman chemistry, which requires a free primary amino group not present in pyro-glutamic acid. The enzyme pyro-glutamate aminopeptidase can restore a free N-terminus by cleaving off the pyro-glutamate residue.

As used herein, a "purification process" refers to one process or a series of processes intended to isolate a protein from a complex mixture. The protein may consist of one or more isoforms i.e. exhibit heterogeneity. The term "purification process" encompasses without limitation protein and antibody purification. The starting material is typically a cell culture (e.g. mammalian cell culture, yeast culture or microorganism culture) and the various steps in the purification process may release the protein from a matrix that confines it, separate the protein and non-protein parts of the mixture, and finally separate the desired protein from all other proteins. In the case the protein is an antibody, the typical separation comprise protein A affinity chromatography, cation exchange chromatography, anion exchange chromatography, hydrophobic interaction and/or hydroxyapatite chromatography.

The term "antibody" as used herein refers to an immunoglobulin molecule comprised of four protein chains, two heavy (H) chains and two light (L) chains interconnected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibody includes, for example, polyclonal antibodies, monoclonal antibodies, Fab and single chain Fv (scFv) fragments thereof, bispecific antibodies, heteroconjugates, human and humanized antibodies. Such antibodies may be produced in a variety of ways, including hybridoma cultures, recombinant expression in bacteria or mammalian cell cultures, and recombinant expression in transgenic animals. Also antibodies can be produced by selecting a sequence from a library of sequences expressed in display systems such as filamentous phage, bacterial, yeast or ribosome. There is abundant guidance in the literature for selecting a particular production methodology, e.g., Chadd and Chamow, Curr. Opin. Biotechnol., 12:188-194 (2001). The choice of manufacturing methodology depends on several factors including the antibody structure desired, the importance of carbohydrate moieties on the antibodies, ease of culturing and purification, and cost. Many different antibody structures may be generated using standard expression technology, including full-length antibodies, antibody fragments, such as Fab and Fv fragments, as well as chimeric antibodies comprising components from different species.

The term "pharmaceutical product" as used herein means a dosage form comprising an active pharmaceutical ingredient (API) suitable for administration to a mammal, such as a human subject, which dosage form may contain suitable carriers and/or excipients and being used in clinical trials or approved for marketing by a national, regional or international authority. Pharmaceutical products comprising a protein, e.g. protein or antibody, prepared by any one of the methods of the present invention, may be prepared by conventional techniques, e.g. as described in Remington: The Science and Practice of Pharmacy 1995, edited by E. W. Martin, Mack Publishing Company, 19th edition, Easton, Pa. The pharmaceutical products may appear in conventional forms, for example capsules, tablets, lyophilized cakes or powders, aerosols, solutions, suspensions or topical applications, in particular as injections, such as subcutaneous or intravenous injections. The pharmaceutical product may be found in a variety of pharmaceutical acceptable formulations and may be combined with one or more physiologically acceptable carriers. The pharmaceutical carrier or diluent employed may be a conventional solid or liquid carrier or diluent. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, sterols, fatty acids, fatty acid amines, polyoxyethylene, isotonic buffer solutions, water and sterile saline solution.

DRAWINGS

FIG. 1: This Figure shows a schematic representation of the mechanism of pyro-glutamic acid formation during cyclization of N-terminal glutamine and N-terminal glutamic acid.

Figure 2:
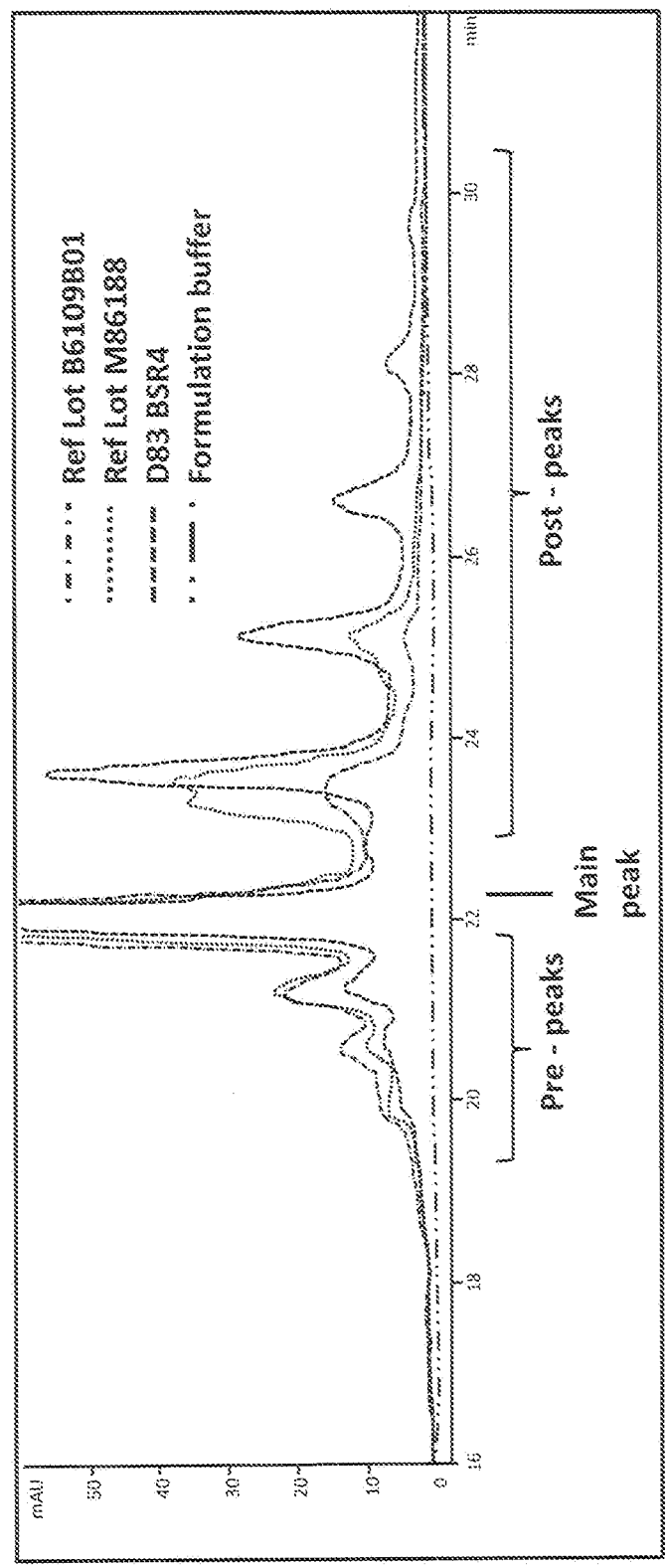

FIG. 2: This Figure shows cation exchange high performance liquid chromatography (IEX-HPLC) profiles of two commercially available Rituximab batches Ref Lot M86188 and Ref Lot B6109B01, as well as herein produced D83 BSR4 Rituximab preparation. pre-peaks, main-peak and post-peaks are indicated in the chromatogram profile. The main-peak was found to consist of Rituximab molecules lacking the two C-terminal lysine residues and having all 4 glutamine residues converted into pyro-glutamate. The significant differences in the appearance of the post-peaks of the commercially available Rituximab antibody preparations, as compared to the herein produced D83 BSR4 Rituximab preparation, was found to be caused primarily by incomplete cyclization of N-terminal glutamine residues.

Figure 3:
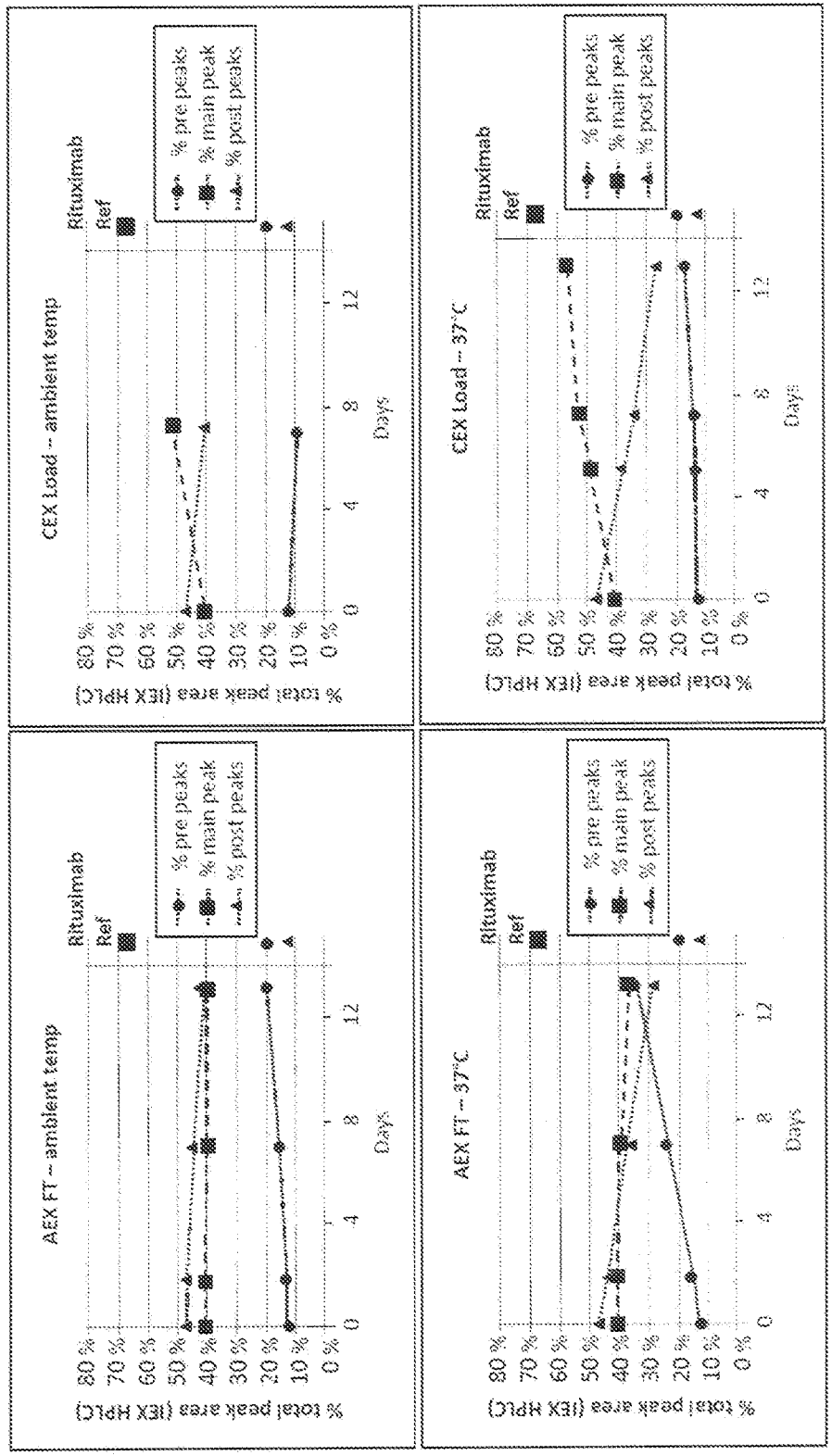

FIG. 3: This Figure shows four graphs representing the correlation between the total peak area in AEX (anion exchange) and CEX (cation exchange) and time of incubation at different temperatures. Top graphs correspond to ambient or room temperature incubation and bottom graphs to 37° C. incubation. FT corresponds to Flow-through of the chromatography.

Figure 4:
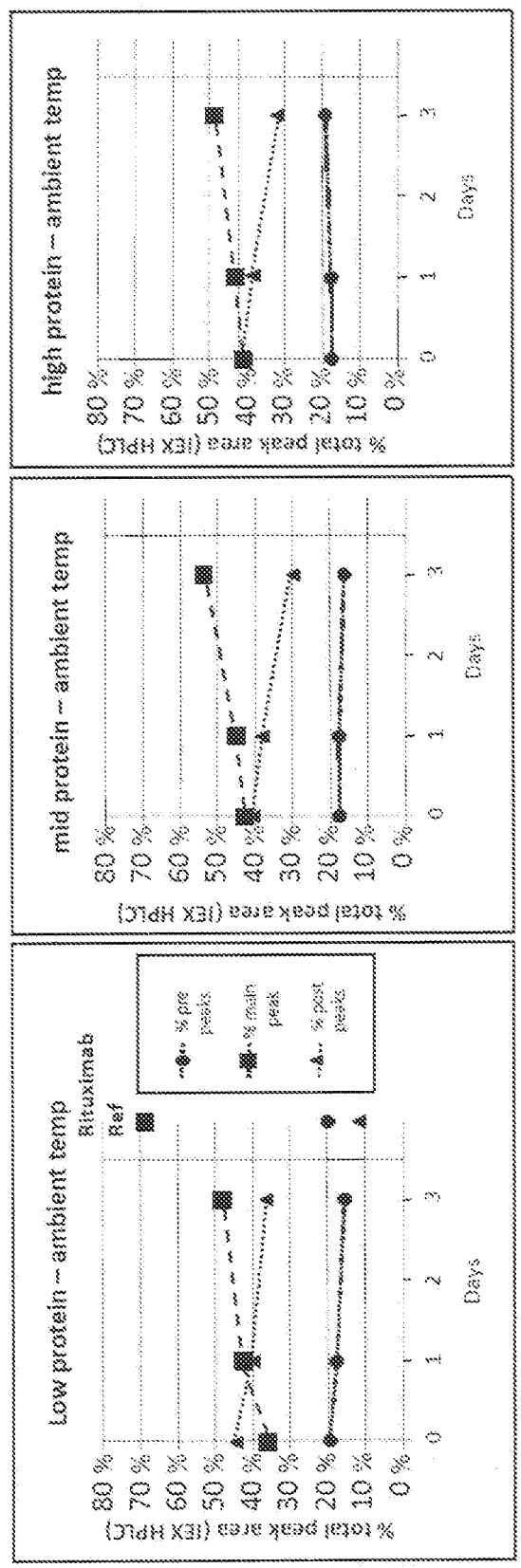
Figure 4:
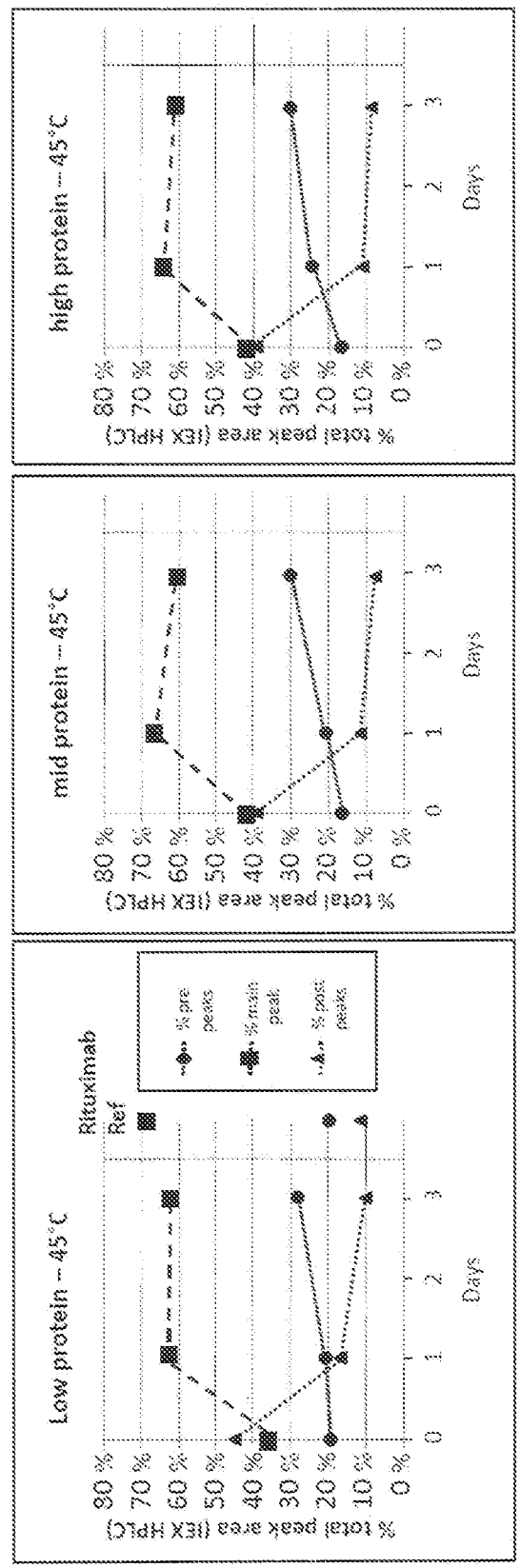

FIG. 4: This Figure shows the kinetics of conversion of the Rituximab post-peaks isoforms into the main-peak isoform at ambient temperature (top panels), at 37° C. (middle panels) and at 45° C. (bottom panels) at low protein concentration (1.85 mg/mL; left panels), at middle protein concentration (3.7 mg/mL; middle panels) and at high protein concentration (9.25 mg/mL; right panels) in a solution with addition of sodium phosphate to 35 mM and titrated to pH 6.25.

Figure 5:
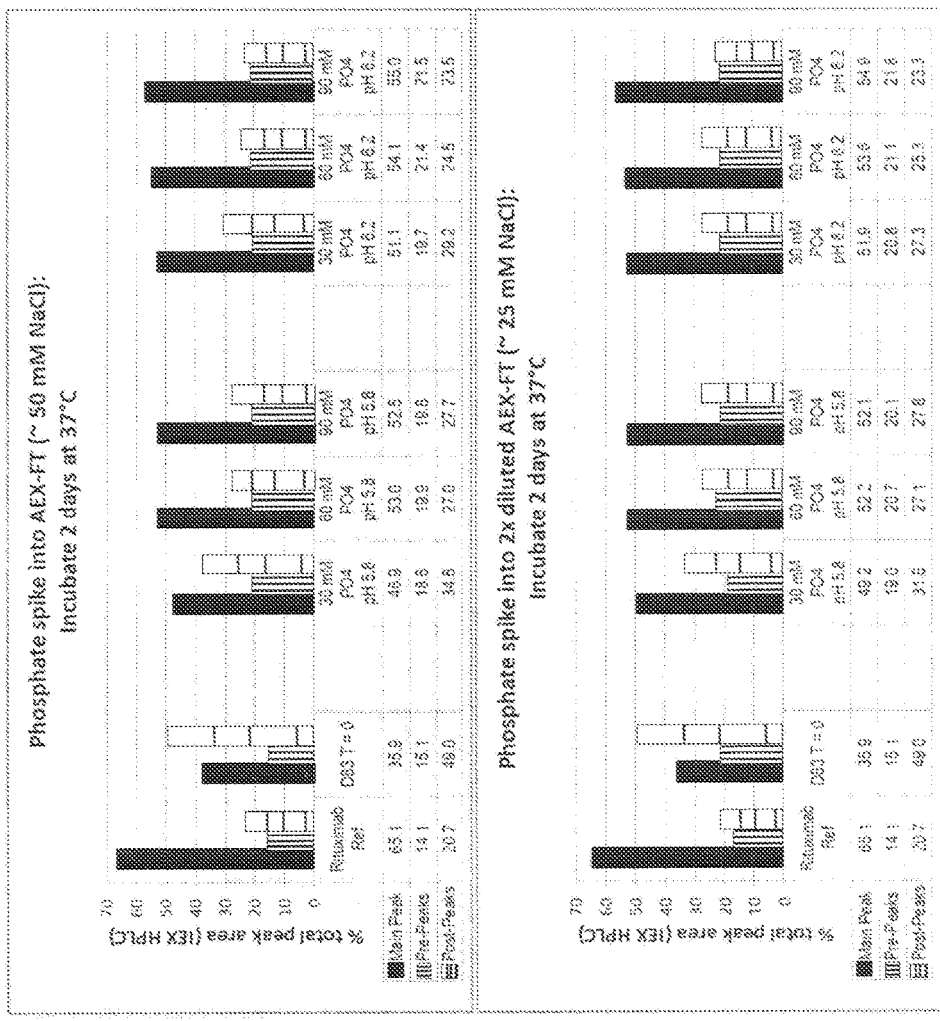

FIG. 5: This Figure shows the effect of different phosphate concentration (30, 60 and 90 mM), sodium chloride concentrations (50 and 25 mM) at pH 5.8 and 6.2 on the conversion kinetics of the Rituximab post-peaks isoforms into the main-peak isoform.

DETAILED DESCRIPTION OF THE INVENTION

The present inventors have found that by introducing a step of incubation/conversion of N-terminal glutamine and/ or glutamic acid residues to pyro-glutamic acid during a purification process of a protein having an N-terminal glutamine and/or glutamic acid residue, the level of heterogeneity can be manipulated, such as reduced to desired levels and at the same time increase the yield of the desired protein.

N-terminal glutamine and glutamic acid of a protein can undergo cyclization forming a pyro-glutamate as shown in FIG. 1. During cyclization of glutamine the N-terminal primary amine (positively charged at a neutral pH) is converted to a neutral amide, resulting in a change of the net charge of the protein. The reaction is accompanied by a loss of ammonia (17 Da) and consequently, the lack of cyclization may be detected as basic variants by cation exchange chromatography, since the main peak is typical the fully cyclized species or as late-eluting peaks by reversed-phase HPLC due to the increased hydrophobicity after the loss of the N-terminal amine.

Cyclization of glutamic acid occurs via the carboxyl group of the side chain and the N-terminal amine, forming a neutral amide and releasing water (18 Da). The net charge remains the same because one acidic and one basic group condense in the reaction, however, the loss of two charged residues increases the hydrophobicity of the molecule, allowing detection by reversed-phase HPLC.

Since many human antibodies contain a glutamic acid and/or a glutamine residue at their N-terminus, pyro-glutamate formation therefore could occur during preparation of many clinically significant antibodies and very often leads to heterogeneity of the expressed antibody, which may differ from batch to batch due to slight variations in production and purification conditions. The same applies to proteins, including polypeptides as this is a significant problem in production of proteins in large scale, such as industrial scale.

In a first aspect the present invention concerns a method for conversion of an N-terminal glutamine and/or glutamic acid residue of a protein to pyro-glutamic acid within a purification process, comprising a step of incubating the protein under conditions to promote cyclization of the N-terminal glutamine and/or glutamic acid residue.

In a second aspect the present invention concerns a method for purification of a protein containing an N-terminal glutamine and/or glutamic acid residue, the method comprising a step of conversion of the N-terminal glutamine and/or glutamic acid residue of said protein to N-terminal pyro-glutamic acid. Such conversion is done under conditions to promote cyclization of the N-terminal glutamine and/or glutamic acid residue.

As used herein the purification process may be performed in accordance with methods known in the art and will vary depending on the specific protein. Protein purification schemes have been predicated on differences in the molecular properties of size, charge and solubility between the protein to be purified and undesired protein contaminants. Protocols based on these parameters include size exclusion chromatography, ion exchange chromatography, differential precipitation and the like.

Processes for purifying antibodies are generally based on affinity chromatography for capture, typically Protein A affinity chromatography. Protein A affinity chromatography refers to the separation or purification of substances and/or particles using protein A, where the protein A is generally immobilized on a solid phase. The Protein A affinity chromatography process is typically followed by ion exchange and/or hydrophobic interactions and/or mixed mode chromatography steps. Such processes generally also include at least two virus reduction steps, typically reduction by low pH in elution from the affinity step and implementation of a virus filter in a suitable position of the process. Impurities removed during antibody purification processes include half antibodies, antibody fragments, dimers, and aggregates, DNA, virus, HCP (host cell proteins), Protein A leakage, endotoxin and other relevant impurities.

In an embodiment of the present invention the protein is selected from an enzyme, a hormone or an antibody. Suitable examples of a protein include any protein that contain one or more N-terminal glutamine and/or glutamic acid residue, including bacteriorhodopsin, fibrinogen, collagen, kinines, Neurotensin, Gastrin, Apelin and Orexin A an antibody or antibody fragments. Examples of antibodies include, without limitation, Trastuzumab, Infliximab, Basiliximab, Daclizumab, Adalimumab, Omalizumab, gemtuzumab, Rituximab, Bevacizumab, Cetuximab, Ofatumumab, Veltuzumabor Ocrelizumab Panitumumab, Ranibizumab, Ibritumomab, Tiuxetan, Abciximab, Eculizumabe, Alemtuzumab, Ozogamicin, Efalizumab, Palivizumab, Natalizumabf, Omalizumab and Tocilizumab.

In a further embodiment of the present invention the antibody is Trastuzumab having the light chain sequence of SEQ ID NO:3 and heavy chain sequences SEQ ID NO:4 and Bevacizumab having the light chain sequence of SEQ ID NO:5 and heavy chain sequences SEQ ID NO:6.

In a still further embodiment of the present invention the antibody is an anti-CD20 monoclonal antibody. Suitable examples of anti-CD20 antibodies include Rituximab, Ofatumumab, Veltuzumab or Ocrelizumab.

In a preferred embodiment of the present invention the antibody is a sequence identical to Rituximab, such as Rituximab.

In a still further embodiment the protein comprises a sequence identical to the light and heavy chain sequences of Rituximab, that is to the sequence of SEQ ID NO:1 and SEQ ID NO:2, respectively.

In a still further embodiment of the present invention the protein comprises a sequence having at least 90% identity, such as 95%, 97%, 98%, 99% identity to SEQ ID NO:1 and having at least 90% identity, such as 95%, 97%, 98%, 99% identity to SEQ ID NO:2.

In a still further embodiment of the present invention the protein has from 1 to 4 N-terminal glutamine and/or from 1 to 4 N-terminal glutamic acid residues before conversion. Thus, if the protein is a single chain protein it may either contain one N-terminal glutamine residue or one N-terminal glutamic acid residue. However, if the protein consists of more than one subunit it may contain one N-terminal glutamine residue and one N-terminal glutamic acid residue or two N-terminal glutamine residues or two N-terminal glutamic acid residues. As explained above antibodies comprise four polypeptide chains (i.e. subunits), two heavy (H) chains and two light (L) chains interconnected by disulfide bonds. Each heavy chain sequence may either encode one N-terminal glutamine residue or one N-terminal glutamic acid residue. Similarly, each light chain sequence may either encode one N-terminal glutamine residue or one N-terminal glutamic acid residue. Accordingly, in further embodiments the protein is an antibody having 2 or 4 N-terminal glutamine and/or glutamic acid residues to be converted according to the method of the present invention, selected from 2 N-terminal glutamine residues, 4 N-terminal glutamine residues, 2 N-terminal glutamic acid residues, 4 N-terminal glutamic acid residues, or 2 N-terminal glutamine residues and 2 N-terminal glutamic acid residues.

Conversion of N-terminal glutamine and/or glutamic acid residues to pyro-glutamic acid may occur spontaneously or it can be aided by an enzyme, such as glutaminyl cyclase.

Glutaminyl cyclase has been implicated in glutamine and glutamic acid cyclization for various peptide hormones and proteins and the enzymatic activity has been detected in different tissues. Spontaneous cyclization of glutamine and glutamic acid in purified antibodies stored at elevated temperatures has also been detected (Schilling et al., FEBS Lett., 2004, 563, 191-196; Kumar and Bachhawat, Current Science, Vol. 102, No. 2, 25 Jan. 2012).

In an embodiment of the present invention the conversion of N-terminal glutamine and/or glutamic acid residues to pyro-glutamic acid is a non-enzymatic conversion. Typically, the non-enzymatic conversion takes place at elevated temperatures, for suitable time periods, and also pH variations may contribute to the conversion. Any one of these parameters is considered an embodiment of the present invention as well as any combination of two or three of these parameters.

Suitable temperatures for conversion of N-terminal glutamine and/or glutamic acid residues to pyro-glutamic acid are in the range from 20-50° C., such as from 25-45° C., such as from 35-40° C., e.g. 37° C. Suitable time-periods for conversion of N-terminal glutamine and/or glutamic acid residues to pyro-glutamic acid are in the range from 4 to 120 hours, such as from 12 to 96 hours, such as from 24 to 72 hours, for instance from 8 to 48 hours.

Suitable pH ranges for conversion of N-terminal glutamine and/or glutamic acid residues to pyro-glutamic acid are in the range from 3.5-9.0, such as from 4.0-8.0, such as from 4.5-7.5, such as from 5.0-7.0, such as from 5.8-6.5, for instance at pH 6.2.

In a typical embodiment of the present invention the conversion takes place at a temperature of 20-50° C. for 4 to 120 hours, such as at a temperature of 30-45° C., e.g. 37-40° C. for 12 to 72 hours.

Non-enzymatic conversion of N-terminal glutamine and/or glutamic acid residues to pyro-glutamic acid may occur in a number of different media. Suitable media in which the protein is in solution or suspension may be selected from water, cell media, a buffer, such as a phosphate buffer, a Tris-HCl buffer, or an ammonium carbonate buffer. The conversion can also take place while the protein is bound to a chromatography resin or membrane, during the purification process.

Typically, non-enzymatic conversion of N-terminal glutamine and/or glutamic acid residues to pyro-glutamic acid may occur in a solution such as a phosphate buffer.

In a still further embodiment of the present invention the conversion is carried out in the cell media.

In a further embodiment of the present invention the conversion is carried out in a buffer, such as in a phosphate buffer or in an ammonium carbonate buffer.

Typically, non-enzymatic conversion of N-terminal glutamine and/or glutamic acid residues to pyro-glutamic acid may be performed on a protein derived from a large-scale production bioreactor that may hold more than 50 L of cell medium, after it has been harvested and partly purified. The conversion may typically be performed in a volume of from 10 ml to 10 L under static conditions or with moderate agitation and in an embodiment of the present invention the conversion is carried out in a volume of at least 10 ml.

Particular suitable media for non-enzymatic conversion of N-terminal glutamine and/or glutamic acid residues to pyro-glutamic acid are media comprising a concentration of buffer from 5 to 150 mM, such as from 10 to 125 mM, such as from 25 to 100 mM. The buffer may also contain a salt, such as NaCl, having a concentration in the range of from 5 to 150 mM, such as from 10 to 125 mM, such as from 25 to 100 mM, such as from 50 to 85 mM.

In a still further embodiment of the present invention the concentration of the buffer for non-enzymatic conversion of N-terminal glutamine and/or glutamic acid residues to pyro-glutamic acid is selected from the range of from 20 mM to 150 mM. In a typical embodiment of the present invention the concentration of the buffer is about 90 mM.

Particular preferred buffers are a 35 mM phosphate buffer with 75 mM NaCl at pH 3.5, a 35 mM phosphate buffer with 75 mM NaCl at pH 6.2, a 100 mM Tris-HCl buffer at pH 7.0, a 100 mM ammonium carbonate buffer at pH 8.6, a 35 mM phosphate buffer at pH 6.2, a 35 mM phosphate buffer with 75 mM NaCl at pH 6.2, a 60 mM phosphate with 50 mM NaCl at pH 6.2, a 60 mM phosphate buffer with 25 mM NaCl at pH 6.2, a 90 mM phosphate buffer with 25 mM NaCl at pH 6.2 or a 90 mM phosphate buffer with 50 mM NaCl at pH 6.2.

The rate of conversion of N-terminal glutamine and/or glutamic acid residues to pyro-glutamic acid may vary depending on the selected buffer, the temperature at which the conversion takes place and the period of time for which the conversion is allowed to proceed. The skilled person will know to identify conditions that lead to optimal conversion without resulting in degradation or unwanted post-translational modifications. In many cases it will be an advantage to get as much N-terminal glutamine and/or glutamic acid converted to pyro-glutamic acid as possible.

In an embodiment of the present invention the conversion from N-terminal glutamine and/or glutamic acid to pyro-glutamic acid reaches at least 50% i.e. at least 50% of the N-terminal glutamine and/or glutamic acid in the protein is pyro-glutamic acid. For instance, a protein or antibody having two N-terminal glutamine residues may result after conversion in a heterogeneous composition comprising the protein with 0, 1, or 2 pyro-glutamic acid(s), as long as the total number of pyro-glutamic acid residues in the protein composition is 50% or more.

In a further embodiment of the present invention conversion from N-terminal glutamine and/or glutamic acid to pyro-glutamic acid reaches at least 53% such as from 53% to 68%.

In a still further embodiment of the present invention conversion from N-terminal glutamine and/or glutamic acid to pyro-glutamic acid reaches at least 68% such as at least 75%, such as at least 80%, such as at least 85%, such as at least 90%, such as at least 95%, such as at least 99%.

The skilled person knows to identify and measure the amount of N-terminal glutamine and/or glutamic acid that have been converted into pyro-glutamic acid. Nevertheless, suitable methods for measuring the levels of pyro-glutamic acid formation are described in Lyubarskaya et al. 2006 (Analytical Biochemistry 348, 24-39) and in Dick et al. 2007 (Biotechnology and Bioengineering, Vol. 97, No. 3, Jun. 15, 2007). Direct determination of the cyclized N-terminal glutamine has also recently been accomplished using electrospray Q-TOF mass spectrometry (Gadgil et al., 2006 J. Am. Soc. Mass Spectrom. 17: 867-872.).

As described above, processes for purifying antibodies are generally based on affinity chromatography, typically protein A affinity chromatography, followed by ion exchange chromatography steps and include virus reduction steps in suitable positions of the process.

In a further embodiment of the method of the present invention the method further comprises the steps: a protein A capture with a suitable resin, an anion exchange chromatography and a cation exchange chromatography with a suitable resin wherein the step of conversion takes place before the cation exchange chromatography step, preferably immediately before the cation exchange chromatography step.

In a still further embodiment of the method of the present invention the method comprises the steps:
(a) protein A capture with a suitable resin,
(b) a viral inactivation at low pH,
(c) an anion exchange chromatography,
(d) the conversion of the N-terminal glutamine and/or glutamic acid of the protein to pyro-glutamic acid,
(e) a cation exchange chromatography with a suitable resin and gradient elution to separate product isoforms,
(f) a viral filtration, and
(g) an ultrafiltration/diafiltration (UF/DF).

In a still further embodiment of the method of the present invention steps (a)-(g) are followed in that specific order.

In a further embodiment of the method of the present invention a step of passive cooling is inserted after step (d), typically before step (e).

In the context of the present invention the protein A capture step a) may be performed using any suitable protein A resin filter or media. Protein A is a bacterial cell wall protein that binds to mammalian IgGs primarily through their Fc regions. In its native state, protein A has five IgG binding domains as well as other domains of unknown function. There are several commercial sources for protein A resin. The skilled person knows what could be a suitable protein A resin filter or media and that also could be a modified protein A resin, filter or media. Nevertheless, suitable protein A resin, filter or media include, but are not limited to, MabSelect™ Sure from GE Healthcare and ProSep Ultra Plus™ from Millipore. A non-limiting example of a suitable column packed with MabSelect™ that can be used for larger purifications can for example be a 20 cm×21 cm column whose bed volume is about 6.6 L. Regardless of the column, the column can be packed using a suitable resin such as MabSelect™ or ProSep Ultra Plus™.

In the context of the present invention the protein A capture step is typically performed in bind/elute mode by loading a clarified harvest solution onto the resin that binds the protein. The skilled person also knows what could be suitable wash conditions for removing impurities from the protein A resin or media. Nevertheless, washing buffers are often selected from buffers comprising from 20-100 mM Tris and from 20 to 1.0M NaCl having a pH of from 7.0-8.0. One example of a suitable elution buffer may be an elution buffer comprising about 200 mM acetate, 50 mM NaCl and having a pH of about 3.5.

Proteins may be expressed in a variety of cells including bacteria such as *E. coli* and *Bacillus*, yeast such as *Saccharomyces*, *Pichia*, *Aspergillus*, *Fusarium* and *Kluyveromyces*, Algae, plant cells, insect cells and mammalian cells such as CHO (Chinese Hamster Ovary) cell, hybridomas, BHK (Baby Hamster Kidney) cell, myeloma cell, HEK-293 cell, human lymphoblastoid cell and a mouse cell. Many complex proteins such as antibodies are often expressed in CHO cells, Murine myeloma cells such as NSO and NS1 cells or in human embryonic retinoblast cells such as PER.C6™. Since such mammalian cells contain endogenous retroviral-like particles, a retroviral inactivation step such as step b) is required for mammalian cells-based protein production intended for clinical use. The skilled person knows how to perform retroviral inactivation step. Nevertheless, viral inactivation is often performed on the eluate from the Protein A capture step by lowering the pH of the eluate from the Protein A capture step. Thus, the pH of the eluate may be lowered to a pH in the range of from 3.0-4.0 for a period of from 5 minutes to 24 hours, such as from 3.1 to 4, for instance from 3.2 to 4, such as from 3.3 to 4, for instance from 3.4 to 4, such as from 3.5 to 4, for instance from 3.6 to 4, such as from 3.7 to 4, for instance from 3.8 to 4, such as to a pH of 4 or from 3 to 3.9, such as from 3.1 to 3.9, for instance from 3.2 to 3.9, such as from 3.3 to 3.9, for instance from 3.4 to 3.9, such as from 3.5 to 3.9, for instance from 3.6 to 3.8, for instance to a pH of 3.6.

As stated above, the eluate from the protein A capture step may be kept at either at these pH values from a period of from 5 minutes to 24 hours such as from 10 minutes to 240 minutes, such as for instance from 20 to 90 minutes and the eluate from the Protein A affinity purification step may be filtered prior to said lowering of the pH value and/or after the readjustment of pH. At the end of the low pH viral inactivation step, the product may be neutralized and adjusted as necessary for forward processing. For instance the pH of the eluate may be adjusted to a pH of from 7.5 to 8.5.

The protein A capture step may be followed by an anion exchange chromatography step operated in the column mode at a certain flow rate or in batch operation mode, by submerging the ion exchange resin into the mildly agitated sample solution and further exchanging liquid media by filtration subsequently. However, in a preferred embodiment this anion exchange chromatography step c) is an anion chromatography step operated in flow-through mode. In this regard the skilled person knows how to define suitable conditions of pH and ionic strength for loading the first ion exchanger, which conditions result in retaining the antibody in the flow through whilst the inactivated viral particles and other impurities are bound to the anion resin and thus removed from the antibody solution.

Examples of suitable anion exchange chromatography resin, filter or media are known in the art and include agarose-based resins and beads, dextran beads, polystyrene beads and polystyrene/divinyl-benzene resins. Preferably, the anion exchange resin is a quaternary amine-based anion exchanger mounted on an agarose matrix such as e.g. Sepharose CL-6B or Sepharose Fast Flow (FF) from Amersham-Biosciences/Pharmacia. Examples of such are Sepharose Q from Amersham-Biosciences/Pharmacia, Sartorius Sartobind Q or Pall Mustang Q. A preferred anion exchange material is Q-Sepharose Fast Flow resin from GE Healthcare.

The equilibration buffer in the anion exchange chromatography according to the present invention preferably has a salt concentration of a displacer salt such as e.g. sodium chloride in the range of from 1 to 150 mM, more preferably of from 5 to 110 mM, most preferably of from 20 to 100 mM salt. The pH of the equilibration buffer is preferably in the range of pH 6.5 to pH 9.0, more preferably is in the range of pH 7.5 to pH 8.5, most preferably is in the range of pH 7.9 to pH 8.2. The equilibration buffer according to the present invention preferably contains Tris in the range of 1 to 100 mM, more preferably of from 5 to 50 mM, most preferably of from 10 to 30 mM Tris. Preferably the conductivity of the equilibration buffer according to the present invention is below 10 mS/cm at pH 8.0.

According to the present invention the first anion exchange chromatography step is typically, followed by a pyro-glutamate conversion step to allow for the conversion of un-cyclized N-terminal glutamine and/or glutamic acid residues into pyro-glutamate. Suitable conditions for the conversion of an N-terminal glutamine and/or glutamic acid residue of a protein to pyro-glutamic acid within a purification process has been described above. However, according to the present invention the conversion of N-terminal glutamine and/or glutamic acid residues into pyro-glutamate may be followed by an optional cooling step if the conversion has been performed at a temperature of above about 25° C. This cooling step may be performed by an active cooling process i.e. for example by using a water based cooling process or a flow-through heat-exchanger; or as a passive cooling process i.e. wherein energy-consuming mechanical components like pumps and fans are not used for lowering the temperature. The cooling process may continue until the resulting conversion solution has reached a temperature of about 18 to 30° C. The cooling process may be carried out for period of time in the range of from 1 to 120 hours, such as of from 12 to 96 hours, such as of from 24 to 72 hours, for instance of from 24 to 48 hours. In a preferred embodiment of the present invention the conversion comprise a step of passive cooling for 12 to 72 hours.

At the end of the pyro-glutamate conversion step, the buffer conditions may be adjusted as necessary for forward processing. For instance the pH of the conversion solution may be adjusted to a pH of about pH 5.5 with acetic acid.

According to the present invention a cation exchange chromatography with a suitable resin and gradient elution to separate product isoforms may follow the pyro-glutamate conversion step. Suitable examples on a cation exchanger include S-SepharoseFF or SP-SepharoseHP (Pharmacia), SP-SepharoseFF (Sigma) and Poros HS50 (Applied Biosystems). A preferred cation exchanger is Poros HS50 from Applied Biosystems.

The protein solution from the pyro-glutamate conversion step may be adjusted to a pH of about pH 5.5 with acetic acid and loaded on the cation exchanger. Suitable wash buffers contain sodium acetate in the range of from 5 to 50 mM and NaCl in the range of from 5 to 50 mM and may have a pH in the range of from 5.0 to 7.0. The bound protein may be eluted using gradient elution from 15 to 180 mM NaCl over 13 column washes into numerous fractions. After elution, the protein fractions may be analyzed and pooled.

A special advantage of performing the conversion step before a cation exchange chromatography step lies in the different charge of the conversion species. Thus, the protein molecule wherein the N-terminal glutamine in not fully converted into pyro-glutamic acid is more positively charged. Accordingly, an antibody that for example has 4 N-terminal glutamine residues where one fraction of the antibody has one N-terminal glutamine residue converted into pyro-glutamic acid, and a second fraction with two N-terminal glutamine residues converted into pyro-glutamic acid, and a third fraction with three N-terminal glutamine residues converted into pyro-glutamic acid, and a fourth fraction where all four N-terminal glutamine residues are converted into pyro-glutamic acid will lead to four different isoforms with four different charges. Such different charged isoforms can be separated by cation exchange chromatography and un-preferred isoforms can be removed.

According to the present invention a viral filtration step is performed after the cation exchanger step. Viral inactivation can be achieved via the use of suitable filters. Although certain embodiments of the present invention employ such filtration during the primary recovery phase, in other embodiments it is employed at other phases of the purification process, including as either the penultimate or final step of purification. In certain embodiments, alternative filters are employed for viral inactivation, such as, but not limited to, Viresolve™ filters (Millipore), Zeta Plus VR™ filters (CUNO), Planova™ filters (Asahi Kasei Pharma) and Ultipor DV50™ filter from Pall Corporation. A preferred filter is a Planova 20N parvovirus rated filter.

After the viral filtration the protein solution go through ultrafiltration/diafiltration (UF/DF) for concentration and buffer exchange. Buffer exchange may be performed by tangential flow filtration (TFF) using a 30 kDa molecular weight cut-off membrane and diafiltering into a detergent-free version of the final formulation buffer.

A third aspect of the present invention relates to a method of preparing a protein having an N-terminal pyro-glutamic acid for a pharmaceutical product wherein the method comprises a method for conversion of an N-terminal glutamine and/or glutamic acid residue of a protein to pyro-glutamic acid within a purification process, the purification process comprising a step of incubating the protein under conditions to promote cyclization of the N-terminal glutamine and/or glutamic acid residue.

A fourth aspect of the present invention relates to a method of preparing a protein having an N-terminal pyro-glutamic acid as an API for a pharmaceutical product wherein the method comprises a method for purification of a protein containing an N-terminal glutamine and/or glutamic acid residue, the method for purification comprising a step of conversion of the N-terminal glutamine and/or glutamic acid residue of the protein to N-terminal pyro-glutamic acid under conditions to promote cyclization of the N-terminal glutamine and/or glutamic acid residue.

Any one of the above embodiments in connection with the first or second aspect of the present invention is also an embodiment of the third and fourth aspects.

In one embodiment, the pharmaceutical product comprises an antibody, typically selected from Trastuzumab, Infliximab, Basiliximab, Daclizumab, Adalimumab, Omalizumab, Gemtuzumab, Rituximab, Bevacizumab, Cetuximab, Ofatumumab, Veltuzumabor Ocrelizumab Panitumumab, Ranibizumab, Ibritumomab, Tiuxetan, Abciximab, Eculizumabe, Alemtuzumab, Ozogamicin, Efalizumab, Palivizumab, Natalizumabf, Omalizumab and Tocilizumab. In a preferred embodiment, the antibody is an anti-CD20 antibody.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context. E.g. "a" or "an" means "one or more".

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., the method of conversion of the purification method described herein as comprising a particular step should be understood as also describing methods consisting of that step, unless otherwise stated or clearly contradicted by context).

This invention includes all modifications and equivalents of the subject matter recited in the aspects or claims presented herein to the maximum extent permitted by applicable law.

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLES

Example 1

A CHO producer cell line expressing the Rituximab monoclonal antibody (also known under the trade name Rituxan) was selected and used to produce the Rituximab antibody in a 10 L single use bioreactor with a stirred tank design using a straight fed-batch fermentation process.

Rituximab is a chimeric antibody, with mouse variable domain and human IgG1 heavy chain and Kappa light chain constant regions. Both the heavy and light chains of Rituximab have a glutamine at their N-termini (after removing the secretory signal peptide), and the heavy chains have a lysine at their C-termini. N-terminal glutamines can cyclize to pyro-glutamic acid both by cellular enzymes and chemical conversion, and C-terminal lysine clipping by cellular carboxypeptidases is very common. Both of these modifications reduce the number of positive charges on the protein, and heterogeneity of these N- and C-terminal modifications contribute to a complex cation exchange high performance liquid chromatography (IEX-HPLC) profile (as shown in FIG. 2).

The clarified harvest sample was first loaded onto a protein A affinity chromatography step using a MabSelect SuRe resin and was run in bind/elute mode. The MabSelect SuRe was washed with 5 column volumes of 20 mM Tris, 1M NaCl pH 8.0 and subsequently with 2.5 column volumes of 20 mM Tris, 50 mM NaCl pH 8.0 before the bound Rituximab antibody was eluted using 4.5 column volumes of 200 mM acetate, 50 mM NaCl, pH 3.5±0.1 and subjected to viral inactivation by incubation at low pH for 105±15 minutes at ambient temperature.

After viral inactivation the solution was neutralized to pH 8 using 0.6 M Tris, 50 mM NaCl pH 8.5 and further purified by anion exchange chromatography using Q-Sepharose Fast Flow resin operated in Flow-through mode. This procedure is known to provide good DNA and viral clearance. Based on prior experience, good viral clearance can be expected from AEX-FT at pH 8.0 if conductivity is ≤10 mS/cm. This can be achieved by simple dilution with Water for Injection (WFI), but with the consequence of increasing process volume and thus processing time. To ensure that a simple 2-fold dilution would reliably result in a final AEX load below 10 mS/cm, it was desirable to reduce the NaCl concentration of the protein A wash and elution buffers by half.

The resulting flow-through solution was analyzed by cation exchange high performance liquid chromatography (IEX-HPLC) performed on a Dionex Propac WCX-10 column, using an Agilent high performance liquid chromatography system and compared to two different batches of commercially available Rituximab antibody preparations designated Ref Lot M86188 and Ref Lot B6109B01, as shown in FIG. 2.

Results from the peptide mapping by mass spectrometry of both commercially available Rituximab antibody preparations Ref Lot M86188 and Ref Lot B6109B01, as well as the herein produced D83 BSR4 Rituximab preparation showed that the main-peak of IEX-HPLC assays consisted of a Rituximab molecule lacking the two C-terminal lysine residues and with all 4 glutamine residues converted into cyclized pyro-glutamate. Moreover, the IEX-HPLC analysis revealed a significant difference in the appearance of the post-peaks of the commercially available Rituximab antibody preparations as compared to the herein produced D83 BSR4 Rituximab preparation.

Analysis of the composition of the lots of Rituximab by peptide mapping and mass spectrometry revealed that the differences in appearance of the post-peaks between commercially available Rituximab and the herein produced D83 BSR4 Rituximab preparation were primarily due to incomplete cyclization of N-terminal glutamine.

One way to reduce the amount of post-peak Rituximab isoforms could be to remove and discard product with excess free N-terminal glutamine during the subsequent cation exchange purification step. However, since the post-peak Rituximab isoforms account for up to 50% of the total Rituximab isoforms in preparations such as D83 BSR4, this would reduce yield by almost half.

Therefore, a subsequent experiment was performed to identify optimal conditions that would promote glutamine cyclization of the anion exchange solution at operationally reasonable temperatures to improve the yield of the Rituximab main-peak isoform.

Example 2

The first conditions to test were simply to determine whether either the anion exchange Flow-through solution (AEX FT) or the subsequent cation exchange loading solution (CEX-Load) would promote glutamine cyclization at ambient temperature or at 37° C.

Samples were taken from the end of the anion exchange flow-through step (pH 8) and after preparation for the cation exchange load had been performed (pH 5.5) and aliquoted into replicate tubes for time-points and held at either ambient temperature or at 37° C. Periodically over 13 days, one tube from each condition was transferred to a −70° C. freezer, and at the end of the time course, all samples were thawed and analyzed by IEX-HPLC (FIG. 3). (Fewer aliquots of the CEX load were made for ambient temperature hold).

As shown in FIG. 3, no conversion of the Rituximab post-peaks isoforms into the main-peak isoform was observed when incubating the Rituximab AEX FT solution at ambient temperature or at 37° C. In contrast, when the Rituximab antibody was incubated in the CEX-Load solution Rituximab post-peaks isoforms were found to be converted into the main-peak isoform both at ambient temperature and when incubated at 37° C. However, the conversion rates both at ambient temperature and at 37° C. were found to be rather slow such that the total percent post-peaks was reduced by ~10% after 8 days of incubation, which corresponds to ~20% of the starting amount of post peaks being converted into the main-peak.

Example 3

Higher conversion rates than the ones observed herein have been reported by Dick et al. (2007, Biotechnol, Bioeng. v97 p 544) in the presence of 35 mM phosphate buffer at pH 6.2. Thus, new experiments were performed to investigate the kinetics of the conversion at ambient temperature, 37° C. and 45° C. and also the effect on the conversion rate that the protein concentration might have.

The Rituximab AEX FT solution was spiked with sodium phosphate to 35 mM from a concentrated stock solution and titrated to pH 6.25 with acetic acid, as the most operationally simple approach to implement in a manufacturing process.

The Rituximab AEX FT sodium phosphate solution was divided into 3 aliquots where one was left unchanged at a concentration of 1.85 mg/mL protein while the two others were concentrated 2× (middle panels) and 5× (right panels) to approximately 3.7 and 9.25 mg/mL using a Millipore 30 kDa MWCO spin concentrator. Each sample was filter sterilized with a 0.2 μm syringe filter and sub-aliquoted into Eppendorf tubes for individual time-points. Several replicate aliquots were held at ambient temperature (top row), 37° C. (middle row), and 45° C. (bottom row) for up to 3 days (FIG. 4). At the indicated time-points, one tube from each condition was transferred to 2-8° C., and at the end of the experiment, all samples were analyzed together in the same assay. Each panel shows the proportion of IEX-HPLC pre, main, and post-peaks across the time-course for each incubation condition. For comparison, the proportion of pre, main, and post-peaks for a commercial available Rituximab reference standard is shown in the first graph in each row.

Results showed (FIG. 4) that higher temperature clearly increased the rate of both pyro-glutamic acid conversion and pre-peak formation, although pyro-glutamic acid conversion was always more rapid than pre-peak formation at each condition. At 45° C., the % main-peak reached a maximum of 60-70% by day 1 and began to drop as pre-peak formation outpaced any additional post-peak conversion. At 37° C., conversion was slower and the same maximum % main-peak was reached by day 3. While some conversion was evident at ambient temperature, the conversion rate at this temperature was less than half of the observed at 37° C. No obvious effect of protein concentration was observed at any temperature.

Example 4

Then, the effect of phosphate concentration (30, 60, 90 mM) was evaluated, including variables of pH and dilution factor (i.e. lower [NaCl]) that would be more conducive for loading onto the subsequent cation exchange POROS HS50 column.

The Rituximab AEX-FT solution (D83) was diluted two fold with either 50 mM NaCl (resulting in ~50 mM NaCl final—top panel) or with water for injection (WFI) (resulting in ~25 mM NaCl final—bottom panel) and spiked with sodium phosphate from a concentrated stock to prepare either a 30, 60, or 90 mM final solution, which were titrated to either pH 6.2 or pH 5.8 with acetic acid. These solutions were incubated for 2 days at 37° C. and analyzed by IEX-HPLC as in example 3. For comparison, the same commercial available Rituximab reference standard and the control D83 T=0 samples are shown in each graph.

Results showed (FIG. 5) that after 2 days of incubation at 37° C., higher phosphate concentration resulted in a slightly greater reduction in post-peaks and a higher increase in the main-peak. Likewise, pH 6.2 promoted slightly better conversion than pH 5.8. No apparent differences were seen between using 25 or 50 mM NaCl.

While at this point, all experiments were performed in small tubes under static conditions experiments were repeated in an agitated shake flask model, to be relevant for large scale manufacturing, where mixing with an impeller would be performed to ensure even temperature, over 3 days at 37° C. These results confirmed previous observations obtained in the smaller static model except from conversion kinetics were slightly faster at 90 mM phosphate in the shake flask model.

Example 5

A full scale complete process manufacturing run including nanofiltration and all microbial control measures was performed using a 500 L bioreactor and purified essentially as described in example 1. After incubating the Rituximab antibody for approximately 28 hours at 37° C., it was gradually cooled down to room temperature during 48 hours. The resulting Rituximab solution was loaded onto cation exchange chromatography POROS HS resin and washed 4 column volumes of 15 mM NaCl, 20 mM NaAcetate pH 5.5 and 5.5 column volumes of 15 mM NaCl, 20 mM NaPhosphate pH 6.5. The Rituximab antibody was eluted using a linear gradient from 15 to 180 mM NaCl over 13 column volumes with fraction collection of 0.5 column volumes per fraction. Table 1 below shows the total protein content of fractions 1 to 9 and the IEX-HPLC assay on the individual fractions and on the pooled fractions 1 to 6 as well as for a commercial available Rituximab preparation designated Rituximab Reference.

As can be seen from table 1, the pooled fractions 1 to 6 corresponds to 96% of the totally eluted protein i.e. Rituximab and the % pre, main and post peaks (16.3; 63.0; 20.7) are rather similar to the commercial available Rituximab preparation (20.2; 66.5; 13:4). In other words the Rituximab isoforms composition of the pooled fractions 1 to 6 resembles closely the commercial available Rituximab preparation.

This is significantly different from the results of experiment 1 where the amount of post-peak Rituximab isoforms accounted for up to 50% of the total Rituximab isoforms.

TABLE 1

Analysis of POROS HS50 fractions for manufacturing run (10-0071).

| Sample | Total protein per fraction (g) | % of total protein | IEX HPLC Assay results | | |
|---|---|---|---|---|---|
| | | | % pre peaks | % main peak | % post peaks |
| Fraction 1 | 30 | 10% | 61.9 | 35.1 | 3.0 |
| Fraction 2 | 72 | 25% | 26.9 | 69.3 | 3.9 |
| Fraction 3 | 83 | 28% | 9.0 | 79.7 | 11.3 |
| Fraction 4 | 64 | 22% | 3.3 | 62.8 | 33.9 |
| Fraction 5 | 18 | 6% | 1.6 | 16.7 | 81.7 |
| Fraction 6 | 15 | 5% | 0.0 | 4.6 | 95.4 |
| Fraction 7 | 3 | 1.1% | 0.4 | 4.8 | 94.7 |
| Fraction 8 | 7 | 2.5% | 0.0 | 3.9 | 96.1 |
| Fraction 9 | 1 | 0.3% | | | |
| Pool Fraction 1-6 | | | 16.3 | 63.0 | 20.7 |
| Rituximab Reference | | | 20.2 | 66.5 | 13.4 |

CONCLUSIONS

As shown in Examples 1 to 5 a robust and more reproducible procedure for converting N-terminal glutamine or glutamic acid residues into pyro-glutamic acid at manufacturing scale has been developed. The process is designed to reduce batch-to-batch variation and to make a product that is similar to a commercial available product with regard to ionic profile.

The process is optimized for easy and fast transfer of an anion exchange flow-through solution containing a protein with un-cyclized N-terminal glutamine residues into a composition containing optimal amounts of phosphate and NaCl having a pH of about 6.2 for non-enzymatic conversion of un-cyclized N-terminal glutamine residues into pyro-glutamic acid within a purification procedure.

REFERENCES

Yu et al., 2006. Investigation of N-terminal glutamate cyclization of recombinant monoclonal antibody in formulation development. Journal of Pharmaceutical and Biomedical Analysis 42, 455-463.

Chelius et al., 2006 Formation of Pyroglutamic Acid from N-Terminal Glutamic Acid in Immunoglobulin Gamma Antibodies. Anal. Chem. 78, 2370-2376.

Dick et al., 2007. Determination of the Origin of the N-Terminal Pyro-Glutamate Variation in Monoclonal Antibodies Using Model Peptides. Biotechnology and Bioengineering, Vol. 97, No. 3, June 15, 544-553.

Needleman and Wunsch 1970. Needleman-Wunsch Algorithm for Sequence Similarity Searches. J. Mol. Biol. 48: 443-453.

Rice et al., 2000. EMBOSS: The European Molecular Biology Open Software Suite Trends Genet. 16: 276-277.

Lyubarskaya et al. 2006. Analysis of recombinant monoclonal antibody isoforms by electrospray ionization mass spectrometry as a strategy for streamlining characterization of recombinant monoclonal antibody charge heterogeneity (Analytical Biochemistry 348, 24-39.

Gadgil et al., 2006: Improving mass accuracy of high performance liquid chromatography/electrospray ionization time-of-flight mass spectrometry of intact antibodies. J. Am. Soc. Mass Spectrom. 17: 867-872.

Chadd and Chamow 2001. Therapeutic antibody expression technology. Curr. Opin. Biotechnol., 12:188-194.

Kumar and Bachhawat 2012. Pyroglutamic acid: throwing light on a lightly studied metabolite. Current Science, Vol. 102, No. 2, 25, 288-297.

The invention claimed is:

1. A method for purification of an antibody containing an N-terminal glutamine and/or an N-terminal glutamic acid, the method comprising a step of incubating said antibody under conditions to promote conversion of the N-terminal glutamine and/or an N-terminal glutamic acid of said antibody to N-terminal pyro-glutamic acid, wherein:
the method for purification comprises the steps of a protein A chromatography with a suitable resin and an ion exchange chromatography with a suitable resin,
the conditions to promote the conversion comprise a temperature of 20-45° C. with a pH in the range of 3.5-9.0 for 4 to 120 hours, and
the conversion from N-terminal glutamine and/or glutamic acid to pyroglutamic acid reaches at least 50%.

2. The method according to claim 1, wherein the antibody is an anti-CD20 antibody.

3. The method of claim 2, wherein the anti-CD20 antibody comprises a light chain sequence identical to SEQ ID NO:1 and a heavy chain sequence identical to SEQ ID NO:2.

4. The method of claim 1 wherein the conversion is carried out in the cell media, or in a buffer.

5. The method of claim 4 wherein the concentration of the buffer is selected from the range of from 20 mM to 150 mM.

6. The method of claim 1 wherein the conversion step comprises non-enzymatic conversion of the N-terminal glutamine and/or the glutamic acid to pyro-glutamic acid.

7. The method of claim 1 wherein the antibody has from 1 to 4 N-terminal glutamine residues and/or from 1 to 4 N-terminal glutamic acid residues before conversion.

8. The method of claim 1 wherein the method comprises the steps:
(a) protein A capture with a suitable resin,
(b) a viral inactivation at a pH in the range of from 3.0-4.0,
(c) an anion exchange chromatography,
(d) the conversion of the N-terminal glutamine and/or glutamic acid of the protein to pyro-glutamic acid,
(e) a cation exchange chromatography with a suitable resin and gradient elution to separate product isoforms,
(f) a viral filtration, and
(g) an ultrafiltration/diafiltration (UF/DF).

9. The method of claim 8 comprising a step of passive cooling for 12 to 72 hours after step (d).

10. A method of preparing an antibody having an N-terminal pyro-glutamic acid as an active pharmaceutical ingredient for a pharmaceutical product, the method comprising a purification method of claim 1.

11. The method of claim 1, wherein step of incubating the antibody under conditions to promote conversion takes place for 12 to 96 hours.

12. The method of claim 1 wherein the conditions to promote the conversion comprise a temperature of 30-45° C.

13. The method of claim 1 wherein the conditions to promote the conversion comprise a pH in the range of 5.0-7.0.

14. The method of claim 1 wherein the conditions to promote the conversion comprise a temperature of 37-40° C. and a pH in the range of 8.8-6.5 for 8 to 48 hours.

15. The method of claim 1 wherein the method of purification comprises the steps of a protein A capture with a suitable resin, an anion exchange chromatography and a cation exchange chromatography with a suitable resin, and the step of incubating the antibody under conditions to promote conversion takes place immediately before the cation exchange chromatography step.

16. The method of claim 8, wherein steps (a)-(g) are followed in that specific order.

* * * * *

SEQUENCE LISTING

```
<160> NUMBER OF SEQ ID NOS: 6

<210> SEQ ID NO 1
<211> LENGTH: 213
<212> TYPE: PRT
<213> ORGANISM: Artificial Sequence
<220> FEATURE:
<223> OTHER INFORMATION: Antibody

<400> SEQUENCE: 1

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
```

```
            115                 120                 125
Ala Ser Val Val Cys Leu Leu Asn Asn Phe Tyr Pro Arg Glu Ala Lys
        130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 2
<211> LENGTH: 451
<212> TYPE: PRT
<213> ORGANISM: Artificial Sequence
<220> FEATURE:
<223> OTHER INFORMATION: Antibody

<400> SEQUENCE: 2

Gln Val Gln Leu Gln Gln Pro Gly Ala Glu Leu Val Lys Pro Gly Ala
1               5                   10                  15
Ser Val Lys Met Ser Cys Lys Ala Ser Gly Tyr Thr Phe Thr Ser Tyr
            20                  25                  30
Asn Met His Trp Val Lys Gln Thr Pro Gly Arg Gly Leu Glu Trp Ile
        35                  40                  45
Gly Ala Ile Tyr Pro Gly Asn Gly Asp Thr Ser Tyr Asn Gln Lys Phe
    50                  55                  60
Lys Gly Lys Ala Thr Leu Thr Ala Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Ser Thr Tyr Tyr Gly Gly Asp Trp Tyr Phe Asn Val Trp Gly
            100                 105                 110
Ala Gly Thr Thr Val Thr Val Ser Ala Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Ala Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
```

```
            260                 265                 270
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
      450

<210> SEQ ID NO 3
<211> LENGTH: 214
<212> TYPE: PRT
<213> ORGANISM: Artificial Sequence
<220> FEATURE:
<223> OTHER INFORMATION: Antibody

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 451
<212> TYPE: PRT
<213> ORGANISM: Artificial Sequence
<220> FEATURE:
<223> OTHER INFORMATION: Antibody

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
```

```
            305                 310                 315                 320
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 5
<211> LENGTH: 214
<212> TYPE: PRT
<213> ORGANISM: Artificial Sequence
<220> FEATURE:
<223> OTHER INFORMATION: ntibody

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

-continued

<210> SEQ ID NO 6
<211> LENGTH: 453
<212> TYPE: PRT
<213> ORGANISM: Artificial Sequence
<220> FEATURE:
<223> OTHER INFORMATION: Antibody

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
```

-continued

```
                355                 360                 365
Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
        435                 440                 445

Leu Ser Pro Gly Lys
        450
```